United States Patent [19]
Engelson et al.

[11] Patent Number: 5,135,494
[45] Date of Patent: Aug. 4, 1992

[54] VALVED CATHETER DEVICE AND METHOD

[75] Inventors: Erik T. Engelson, Portola Valley; John R. Daniels, Pacific Palisades, both of Calif.

[73] Assignee: Target Therapeutics, Fremont, Calif.

[21] Appl. No.: 794,776

[22] Filed: Nov. 18, 1991

Related U.S. Application Data

[63] Continuation of Ser. No. 686,310, Apr. 16, 1991, abandoned, which is a continuation of Ser. No. 587,526, Sep. 21, 1990, abandoned, which is a continuation of Ser. No. 499,573, Mar. 26, 1990, abandoned, which is a continuation of Ser. No. 226,674, Aug. 1, 1988, abandoned, which is a continuation-in-part of Ser. No. 83,624, Aug. 7, 1987, Pat. No. 4,813,934.

[51] Int. Cl.$^5$ .............................................. A61M 29/00
[52] U.S. Cl. ........................................... 604/99; 606/194
[58] Field of Search ............................. 604/96-103, 604/164, 170; 606/194; 128/341, 344, 348.1, 207.15, 656-658, 772; 600/16-18

[56] References Cited

U.S. PATENT DOCUMENTS

| | | | |
|---|---|---|---|
| 3,402,717 | 9/1968 | Doherty | 604/99 X |
| 3,460,541 | 8/1969 | Doherty | 128/207.15 |
| 3,548,805 | 12/1970 | Datsenko et al. | 604/97 X |
| 4,276,874 | 7/1981 | Wolvek et al. | 604/96 X |
| 4,315,512 | 2/1982 | Fogarty | 128/344 |
| 4,413,989 | 11/1983 | Schjeldahl et al. | |
| 4,606,347 | 8/1986 | Fogarty et al. | 128/344 |
| 4,616,652 | 10/1986 | Simpson | 128/772 X |
| 4,638,805 | 1/1987 | Powell | 604/97 X |
| 4,646,742 | 3/1988 | Packard et al. | |
| 4,726,374 | 2/1988 | Bales et al. | 128/344 |
| 4,813,934 | 3/1989 | Engelson et al. | 604/99 |

FOREIGN PATENT DOCUMENTS 3246219 10/1981 U.S.S.R. .

Primary Examiner—John D. Yasko
Attorney, Agent, or Firm—Morrison & Foerster

[57] ABSTRACT

A catheter device for accessing an internal body site along a small-diameter vessel path containing branch points in which the path may follow either the larger of smaller-diameter branch vessels. The device includes a catheter having a distal-end inflatable balloon and an distal-end aperture. A guide wire in the device is designed to partially block the aperture at one or more axial wire positions, allowing the balloon to be inflated by fluid infusion into the catheter. In a catheter placement operation, the catheter is advanced along the vessel path toward the selected target site. When the leading end of the catheter encounters a branch point at which the path follows the larger-diameter vessel, the guide wire is moved to a position which partially blocks the catheter aperture, and fluid is infused into the catheter to inflate the balloon. The catheter is then carried by hydrodynamic flow into the larger-diameter vessel. When the catheter end encounters a branch point at which the path follows the smaller diameter of the two branch vessels, the catheter is deflated and the guide wire is manipulated to orient the wire for movement into the smaller vessel.

11 Claims, 3 Drawing Sheets

VALVED CATHETER DEVICE AND METHOD

This application is a continuation of Ser. No. 686,310 filed Apr. 16, 1990 now abandoned which is a continuation of application Ser. No. 587,526 filed Sep. 21, 1990, now abandoned which is a continuation of application Ser. No. 499,573 filed Mar. 26, 1990, now abandoned which is a continuation of application Ser. No. 226,674 filed Aug. 1, 1988 now abandoned, which is a continuation in part of application Ser. No. 083,624 filed Aug. 7, 1987, now abandoned.

FIELD OF THE INVENTION

This invention relates to catheter devices and methods for accessing internal body target sites along a small-vessel path.

BACKGROUND OF THE INVENTION

Catheters are being used increasingly as a means for delivering diagnostic or therapeutic agents to internal target sites, and to perform mechanical functions on vasculatures that can be accessed through the circulatory system. For example, in angiography, catheters are designed to deliver a radiopaque agent to a target site within a blood vessel, to allow radiographic viewing of the vessel and blood flow characteristics near the release site. For the treatment of localized disease, such as solid tumors, catheters allow therapeutic agents to be delivered to the target site at a relatively high concentration, with reduction in drug delivery to non-target sites. Often the target site which one wishes to access is in a tissue, such as brain, liver or kidney, which requires catheter placement along a tortuous path through small vessels or ducts, such as arterial vessels or biliary ducts. Typically, the vessel path will include vessel branch points at which the path may follow either a relatively larger-diameter, higher-flow branch vessel, or a relatively smaller, lower-flow branch vessel.

Heretofore, three general types of catheters have been developed for accessing internal target sites. One type is a torqueable catheter having relatively rigid tube construction and large-diameter lumen. In particular, the catheter tube may be formed as a braided fiber or wire laminate which has high torque properties. The distal portion of the catheter can be made narrower and more flexible by eliminating laminate windings or braid from this portion of the catheter, but this compromises torque transmission. Torqueable catheters of this type are generally too large in diameter and too rigid to be safely advanced through narrow, tortuous vessel or duct paths.

Another type of guidable catheter is a guide-wire catheter which contains a single-lumen catheter used in conjunction with a flexible, torqueable, guide wire which can be moved axially within the catheter. In a typical catheter-placement operation, the wire is advanced along the vessel pathway, using wire torquing to orient the bent tip of the wire along the selected path, i.e., into and through selected branch vessels and/or regions of sharp bends. The catheter is then advanced along the wire with the wire held in place. The wire and catheter are alternately advanced in this manner until the target site is reached. Thereafter, the wire can be removed to allow fluid delivery through the catheter into the site. Since the wire can be both torqueable and quite flexible, and the catheter can be a thin-walled flexible tube, the catheter device is well suited for accessing sites via small-diameter tortuous paths.

Another general class of guidable catheters have a distal-end balloon which can be partially inflated to carry the catheter in the direction of highest blood flow, and therefore along a vessel path having maximum blood flow. The balloon may be further inflated, at a selected target site, for purposes of occluding blood flow, or for anchoring the catheter end at the selected site. Extending the balloon to contact the walls of a blood vessel can also be useful in relaxing spasmodic vessel muscles, resulting in less vessel constriction. Balloon catheters thus have the advantage over guide-wire catheters in that they can take advantage of blood flow for advancing along a vessel pathway, and various advantages relating to balloon contact with vessel walls can be achieved.

One type of balloon catheter has a double-lumen construction, where one lumen communicates with the distal balloon, for transferring fluid to or from the balloon. The second lumen allows delivery of injected material, such as a radio-opaque tracer material or therapeutic agent, into the target site. One advantage of the double-lumen catheter is the ability to inflate the balloon to relatively high pressure, which is particularly useful when the balloon is used for stretching a vessel wall, in a catheter treatment for removing vessel plaque. Also, the catheter can be firmly anchored at the target site when the balloon is in a highly inflated state. The double-lumen balloon catheter, however, is not well suited for guidance along small-diameter, tortuous pathways, since the catheter typically has a relatively large outer shaft diameter, and these shafts are generally relatively inflexible. Alternatively, the two catheter lumens may be made relatively small, but here fluid passage through the lumens is slow and limited to low-viscosity agents. Also, since the catheter is guided by blood flow, the device is limited in use to vessel paths with highest blood flow.

In a second balloon-catheter construction, the catheter has a single-lumen tube which communicates with a slow-leak balloon at the distal tube end. In operation, fluid is supplied through the tube at a slow controlled rate, to maintain the balloon at an inflated condition which promotes fluid-directed movement through the vessel path. The single lumen tube can have a small-diameter, highly flexible construction which permits movement along a small-diameter, tortuous vessel path. The ability to guide the catheter, however, is limited to vessel or duct branches with greater flow, as above, so the catheter is not generally useful for accessing a site against the direction of flow, or along a pathway which includes relatively low-flow branches. Another limitation of the single-lumen catheter is that the slow-leak principle of balloon inflation does not allow for high-flow delivery of fluid material or delivery of particulate suspension at the target site.

A third balloon catheter construction has a single-lumen catheter which communicates with a sealed balloon. The catheter is able to access small-vessel tortuous paths and allows relatively high balloon inflation pressures. The catheter is limited, however, to vessel paths of highest blood flow, and of course cannot be used to deliver fluid to the target site.

SUMMARY OF THE INVENTION

It is a general object of the invention to provide an improved catheter device for accessing a target site along a small-vessel tortuous path.

A related object of the invention is to provide such a device which overcomes or reduces above-discussed problems and limitations associated with prior art guidable catheters.

A more specific object of the invention is to combine advantages of balloon catheters and guide-wire catheters in a single device.

The catheter device of the invention includes a catheter having (a) an inner lumen extending between proximal and distal catheter ends, (b) an inflatable balloon at the distal catheter end which communicates with the inner lumen, and (c) an aperture disposed distally of the communication between lumen and balloon. The balloon may be carried at the distal end of catheter, or along a distal end section of a catheter tube, or formed as an intermediate inflatable section of a catheter tube. The device further includes a guide wire which is designed for axial sliding movement within the catheter lumen. The guide wire and catheter aperture define a valve structure effective to partially block the aperture at one or more selected wire positions, to permit the catheter balloon to be inflated by supplying fluid through the catheter lumen.

In one general embodiment, the catheter aperture is defined by an annular ring mounted in the distal end of the catheter. The ring aperture is dimensioned to receive a distal end segment of the guide wire freely therethrough, with limited wire clearance. Where the catheter is formed of a tube having an inflatable distal end balloon, the ring is positioned at the distal end of the balloon. Where the balloon is disposed along an end section of the catheter tube, the ring is disposed distal to the balloon end section or distal to an opening communicating the catheter tube with the balloon.

In a second general embodiment, the catheter balloon is an inflatable sleeve carried on a distal end segment of the catheter tube, where the catheter lumen communicates with the inflatable sleeve through an opening in the catheter tube. The guide wire in this embodiment has an enlargement which is dimensioned to be moved freely through the catheter with limited clearance, to partially block the interior walls of the catheter lumen. The balloon can be inflated by moving the guide wire enlargement to a position within the catheter tube, just downstream of the opening communicating the lumen and the balloon, and supplying fluid through the tube.

The invention also includes a method for accessing an internal body site along a narrow-vessel tortuous path which includes some branch points in which the path follows the larger-diameter of two branch vessels, and some in which the path follows the smaller diameter of two branch vessels. The method employs a catheter device of the type described in which a single-lumen balloon catheter and a guide wire movable therein define a valve structure which can be manipulated to partially block the distal end of the catheter, for purposes of supplying fluid to and inflating the balloon.

In the accessing method, the guide wire and catheter are advanced along the vessel pathway toward the target site. When a branch point at which the vessel path follows the larger-diameter of two branch vessels is reached, the guide wire is placed in a position to partially close the balloon valve, and the balloon is inflated, allowing the distal end of the catheter to be carried by fluid flow into the larger-diameter vessel. When a branch point at which the vessel path follows the smaller diameter of two branch vessels is reached, the guide wire can be torqued to orient the guide wire tip in the direction of the smaller-diameter vessel, and the catheter then advanced into the smaller vessel, with the catheter balloon preferably in an uninflated state.

The catheter can also be manipulated for balloon inflation at a position along a vessel pathway where vessel constriction is encountered, or to anchor the catheter at the target site.

These and other objects and features of the invention will become more fully apparent when the following detailed description of the invention is read in conjunction with the accompanying drawings.

DETAILED DESCRIPTION OF THE INVENTION

I. Catheter Device Construction

Figure 1:
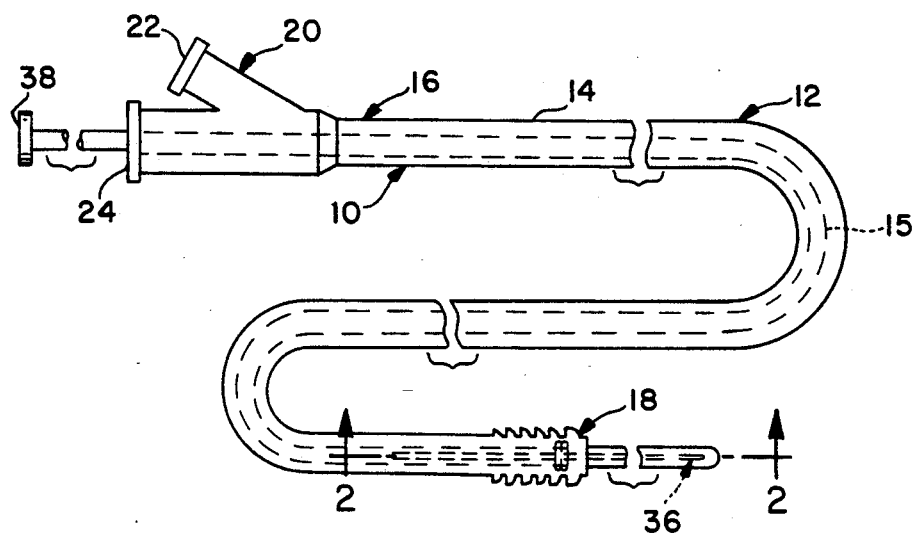
FIG. 1 shows a catheter device constructed according to one embodiment of the invention.
Figure 3:
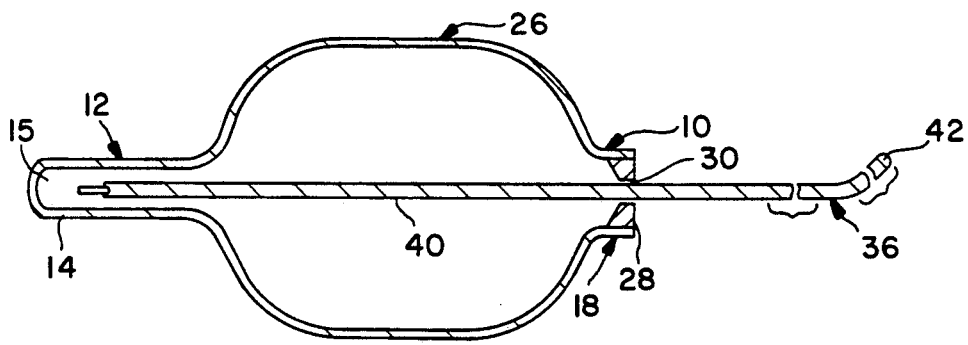
FIG. 3 shows the enlarged distal end section of the FIG. 2 catheter device with the balloon in an inflated condition.
Figure 2:
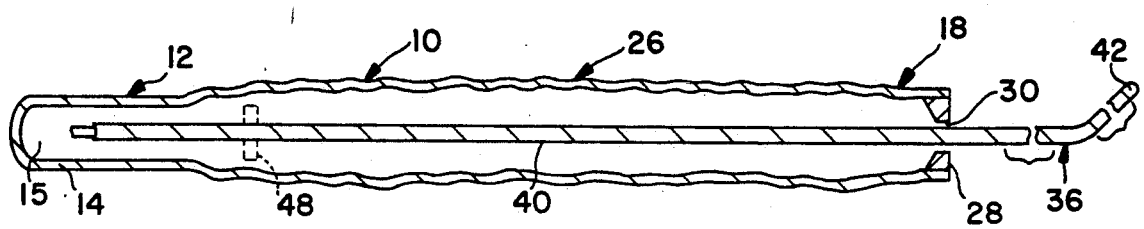
FIG. 2 is an enlarged sectional view taken along line 2—2 of FIG. 1.

FIGS. 1-3 show a catheter device 10 constructed according to one embodiment of the invention. Device 10 includes a catheter 12 composed of a flexible, thin-walled tube 14 having an inner lumen 15 extending between proximal and distal catheter end regions 16, 18, respectively. The proximal catheter end is provided with a syringe fitting 20 through which fluid can be supplied to the catheter lumen through a port 22. The fitting includes an axially extending port 24 also communicating with the catheter's inner lumen. Tube 14 preferably has an inner diameter of approximately 15-60 mils and walls that are approximately 3-15 mils thick. The total tube length is preferably between about 50-300 cm.

With reference now to FIGS. 2 and 3, the distal end of the catheter is provided with an inflatable balloon 26 which forms an intermediate section of the distal end region of tube 14. The balloon is preferably about 0.5 to 2 cm in length, and has a wall section which can be inflated by fluid supply through the catheter lumen, when the distal end of the tube is partially blocked in a manner to be described below. The balloon wall section is preferably formed integrally with the tube, according to known extrusion methods for producing a thin walled-extruded tube with a more flexible distal-end wall section. In particular, the balloon may be formed by inflating the balloon section in a heated condition, then deflating when the balloon wall section has cooled.

Alternatively, the balloon may be formed from a sleeve of elastomeric material, such as silicon rubber, and attached at its opposite sleeve ends to relatively more rigid tube sections. The region along the length of the balloon is also referred to herein as means communicating the catheter lumen with the balloon.

Disposed in the distal end of the catheter tube is an annular plug or ring 28 defining an aperture 30 formed axially in the ring. The ring, which is also referred to herein as means defining aperture 30, is positioned downstream of (on the distal side of) the means communicating the catheter lumen with the inflatable balloon, i.e., distal with respect to the balloon. The ring has an inwardly tapered, frustoconical wall section which acts to guide the guide wire through the central aperture in the ring. The diameter of the aperture is typically about 40-80% of the lumen diameter. The ring may be made of a suitable metallic or nonmetallic material, and can be attached to the catheter tube by heat shrinking, solvent bonding or the like.

The catheter device also includes an elongate, torqueable guide wire 36 which is constructed to extend through the catheter for axial sliding therein. The length of the guide wire is typically at least about 10-50 cm longer than the catheter, such that the distal end of the guide wire, seen in FIGS. 2 and 3, can be extended at least several centimeters beyond the distal end of the catheter, while allowing the proximal end of the wire to be manipulated, such as by torquing, adjacent the proximal end of the catheter. The proximal end of the wire is equipped with a handle 38, such as a pin vice, for applying torque to the wire during a catheter operation.

The guide wire may have a variable or step diameter along its length, typically including a larger-diameter, stiffer proximal region, and one or more smaller-diameter, more flexible distal end regions, giving the wire good torqueability in its more proximal region, and better flexibility and maneuverability along its more distal region where the wire is advanced along small-diameter tortuous pathways. Typical wire dimensions, for a catheter having an lumen diameter of between about 20-50 mils, are a proximal segment extending along all but the last 20-50 cm of wire and having a diameter of between about 18-40 mils, and one or more reduced diameter segments 20-50 cm in length having diameters of between about 8-18 mils.

In addition the distal end portion of the wire may have a substantially constant taper, down to a final wire thickness of about 1-5 mils, for greater distal-end flexibility. This tapered region is preferably encased in a constant-diameter platinum coil, such as coil 40 seen in FIGS. 2 and 3. The guide wire terminates in a bent tip 42 which can be oriented by torquing.

The guide wire is preferably made of stainless steel such as is commercially available from Wytech or National Standard. The tapered tip may be made by a suitable technique, such as by grinding. In the embodiment shown, guide wire 36 is 8-20 mils at its proximal end and tapers down to a 2 mil distal tip over about a 10-20 cm length. The coil is made conventionally of wound 3 mil platinum, tungsten or other suitably radiopaque wire commercially available, e.g., from California Fine Wire Company or Sigmund Cohn. This coil preferably has an inner diameter of 7 mils and a length of approximately 2-20 cm. The coil is attached to guide wire 12 by an appropriate technique, such as soldering or brazing.

The diameter of the distal end section of the wire, including wire coil 40, is preferably about 0.5-2 mils less than that of aperture 30, allowing a distal end portion of the wire to be moved freely (with clearance) through the aperture. At the same time, the limited clearance between the guide wire and aperture forms a valve structure which is effective to partially block the aperture, such that fluid supplied through the catheter will inflate the catheter balloon. The limited clearance between the guide wire is selected so as to allow the balloon to be inflated to a greater (smaller clearance) or lesser (larger clearance) balloon pressure, and/or to allow a desired leakage rate from the balloon in the inflated state.

The guide wire may optionally include an axial enlargement, such as shown in dotted lines at 48 in FIG. 2, which is effective to completely block the catheter aperture, when the guide wire is moved to position the enlargement against the aperture ring. This modification is useful where it is desired to inflate the balloon to a relatively high pressure, such as where the catheter device is used for stretching a vessel for purposes of plaque compression.

In operation, the guide wire is placed in the catheter through port 24 in fitting 20, and threaded through the catheter until the wire's distal end extends from the distal end of the catheter, as shown in FIG. 1. During a catheter placement operation, as will be described in Section II below, it will be advantageous to operate the catheter in an uninflated condition during some phases of operation, and in an inflated operation at other times. To achieve balloon inflation, the guide wire is moved axially into and through aperture 30, and fluid is supplied through the lumen through port 22 in fitting 20, acting to fill and inflate the balloon. Once the balloon is inflated, material is supplied through the catheter under slight pressure to offset fluid leakage through the partially blocked valve.

To deflate the balloon, the guide wire is retracted, to unblock the aperture and cause the fluid in the balloon to leak out the distal end of the catheter, with progressive balloon deflation. Alternatively the balloon can be deflated by withdrawing fluid from the catheter through port 22.

Figure 4:
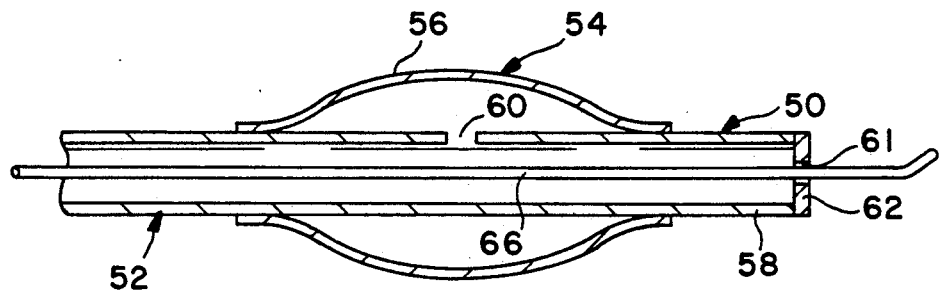
FIGS. 4-6 are enlarged sectional views of the distal end sections of catheter devices constructed according to various alternative embodiments of the invention.

FIG. 4 illustrates a catheter device 50 in which the catheter, indicated at 52, has an inflatable balloon 54 which is formed by an inflatable sleeve 56 secured at its opposite ends to a thin-walled, flexible catheter tube 58. The balloon sleeve may be formed of a thin polymer material, and preferably an elastomeric, stretchable material, such as silicon or latex rubber, or alternatively, a non-stretchable film material, such as polyethylene. Attachment of the sleeve ends to the catheter tube is tube by gluing, heat sealing, or the like, also according to known methods. The advantage of an elastomeric sleeve is that it tends to remain flush with the tube in an uninflated state, and also tends to resist balloon inflation. Therefore, the balloon will tend to deflate itself when fluid pressure in the tube is released.

An opening 60 formed in the catheter tube provides means communicating the balloon with the catheter lumen. Distal to this opening is a ring 62, which defines an aperture 61 in the catheter tube. A guide wire 66 in the device has an outer diameter which, as above, is dimensioned to partially block the aperture when the wire is moved through the ring. This wire thus forms with the ring valve structure for partially blocking the catheter lumen downstream of opening 60. The guide wire may have substantially the same construction as guide wire 36 in device 10. The operation of device 50, in balloon inflating and deflating operations, is substantially identical to that of device 10.

Figure 5:
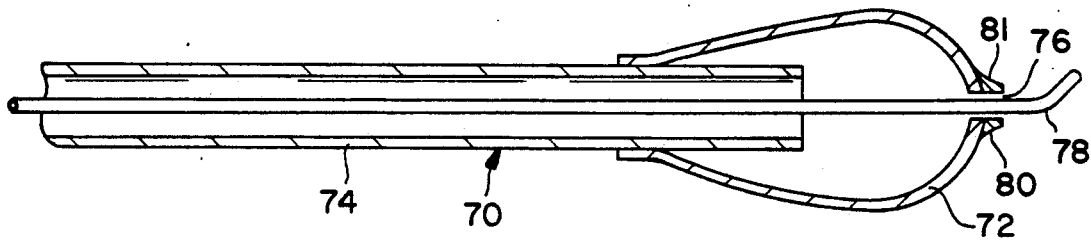

FIG. 5 shows a similar type of catheter device 70 having a distal-end balloon 72 which is attached to and extends from the distal end of the catheter tube, indicated at 74. The distal end of the catheter thus provides the means communicating the balloon with the catheter lumen. The balloon is formed of a membranous or elastomeric sac having a distal opening 76 which is dimensioned to receive the distal end of a guide wire 78 freely therethrough, with limited clearance. The opening is reinforced by a plug 80 whose inner bore with the same diameter as opening 76. This plug, which is preferably a flexible elastomeric material, may be formed integrally with the balloon, or attached to the balloon as by gluing. The opening and plug form a ring which defines a central aperture 81 in the catheter.

Guide wire 78 in the device has an outer diameter which is dimensioned to be received through aperture 81, to partially block the lumen of the catheter tube, when the wire is moved through the tube. The wire and aperture formed in the distal end of the balloon collectively form valve structure for use in inflating the balloon, as above.

Figure 6:
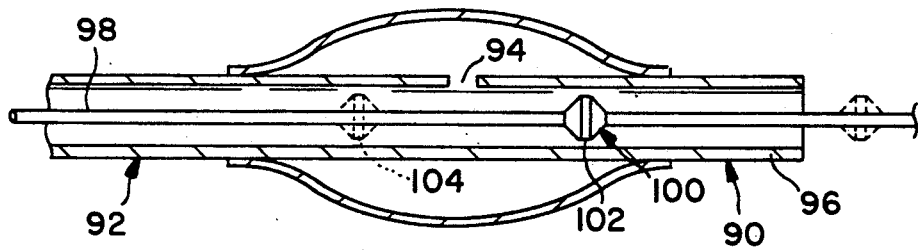

In FIG. 6, a catheter device 90 has a catheter 92 whose tube and distal balloon construction is substantially the same as that of catheter 52 in FIG. 4, where the balloon communicates with the catheter tube lumen through an opening 94 in the catheter tube. Here, however, the aperture is defined by the lumen itself, in the region between opening 94 and the distal end of the catheter tube. This region or aperture is indicated generally at 96 in the figure.

A guide wire 98 in the device has an enlargement 100 which is tapered on either side, as shown, and whose outermost rim 102 is dimensioned to slide freely within the lumen, with a clearance which is effective to partially block the lumen. With the enlargement positioned within the aperture of the catheter, i.e., between opening 94 and the distal end of the catheter tube (solid lines in the figure), the enlargement and aperture form valve structure for partially blocking the aperture. At this position, supplying fluid through the lumen inflates the balloon. With the guide wire moved slightly in a proximal or upstream direction, to place the enlargement at the position shown at 104, the lumen remains partially sealed, but fluid can leak from the balloon, for deflating the balloon.

II. Catheter Accessing Met nod

Figure 7:
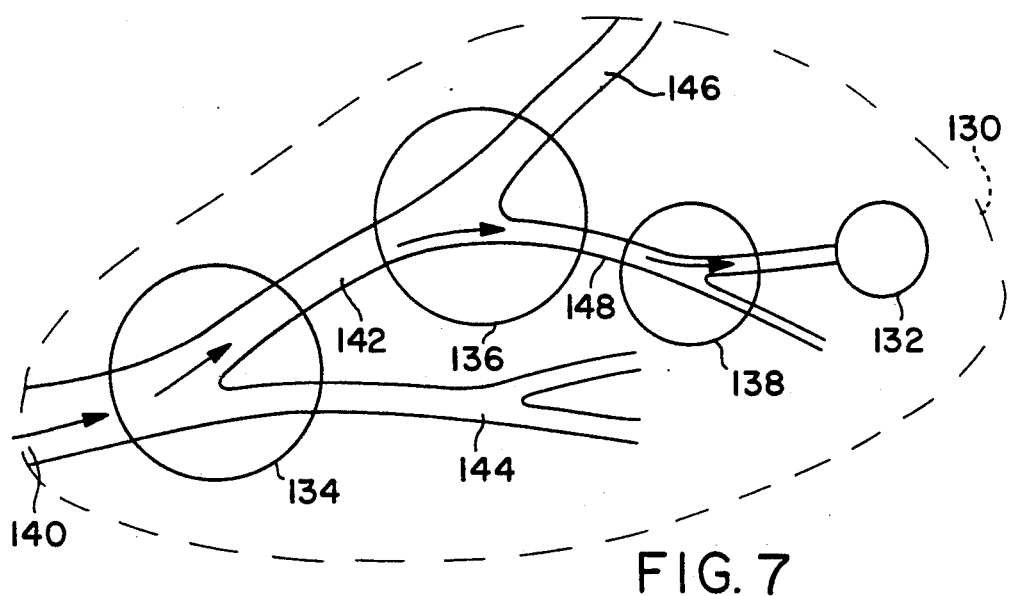
FIG. 7 shows a portion of a small-vessel tortuous path in a target tissue.
Figure 8:
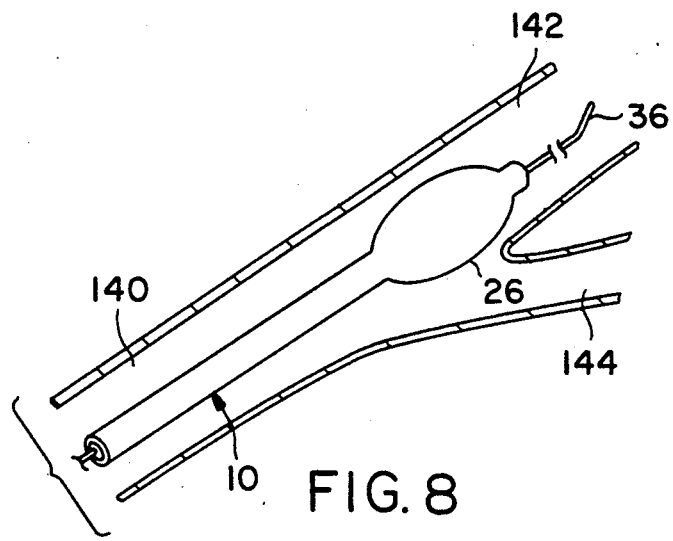
FIG. 8 shows a branch junction region from FIG. 7, in which the path of the catheter follows the larger-diameter of two branch vessels.

The method of accessing an internal body site along a small-vessel, tortuous vessel or duct path, according to the method of the invention, will now be described with reference to FIGS. 7–9. FIG. 7 shows a region of soft tissue 130, such as brain or liver tissue, containing a target site 132 which is to be accessed. The small-vessel path within this tissue region which leads to the target site is shown by arrows in the figure and includes three branch points, indicated at 134, 136, and 138, all supplied by a trunk vessel 140. Each branch point diverges into two branch vessels, such as branch vessels 142 and 144, diverging from vessel 140, and branch vessels 146 and 148 diverging from vessel 142. Often at a branch point along the vessel path, one of the two branch vessels, such as vessels 142 and 146, will have a relatively larger diameter and greater blood volume flow than the other branch vessel, such as vessels 144 and 148.

The method employs a guide-wire catheter device of the type described above in which an inner-lumen balloon catheter balloon catheter and a guide wire movable therein define a valve structure which can be manipulated to partially block the distal end of the catheter, for purposes of supplying fluid to and inflating the balloon. In a typical operation involving a target site accessed through a vascular system, the catheter device is threaded as a unit from an external access site through the vasculature to a region adjacent, but not into the tortuous path region of the target tissue. This is done, in the usual case where the catheter must pass through the cardiac aorta, by first placing a relatively large diameter guiding catheter e.g., about 40 mils inner diameter) from the access site through the aorta and toward the target site. The present catheter and guide wire are then threaded through the guiding catheter past the aorta, where large-vessel diameters and high blood flow volumes make it difficult or impossible to control the movement and position of the catheter. Once beyond the guiding catheter, the catheter and guide wire can be independently controlled to move toward the target site. In general, the path from the access site to the region adjacent the tissue is easily accessible, in that sharp bends, small-lumen vessels, and or soft tissue structure are not encountered.

The distal end of the device is now advanced into the target tissue along the selected path until branch points in the vessels or ducts making up the small-vessel path are encountered, as illustrated in FIG. 7. For purposes of illustration, it is assumed that the catheter has been moved along the path until branch point 134 in FIG. 7 is encountered. Since the selected path follows the larger-diameter, greater-flow branch vessel 142, the catheter can be guided by blood flow, by inflating the catheter balloon and allowing the distal catheter end to flow into the larger vessel, as illustrated in FIG. 8, which shows the catheter device being guided into and through vessel 142. The balloon is inflated, before the branch point is reached by the procedure mentioned above, which involves first moving the guide wire in the device to partially block the catheter aperture, then supplying fluid) through the catheter until a desired degree of inflation is reached. After the catheter's distal end has been carried into the larger-diameter branch vessel, the wire may be further manipulated to open the valve structure, and/or fluid can be withdrawn from the catheter, to deflate the balloon.

Figure 9:
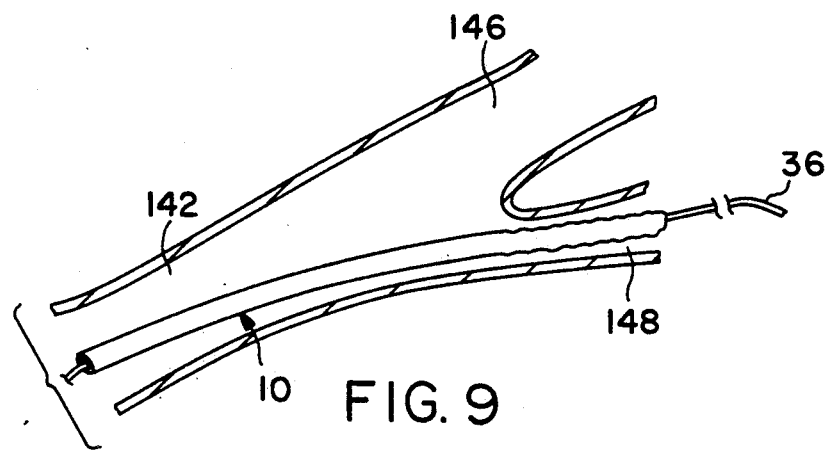
FIG. 9 shows a branch junction region from FIG. 7, in which the path of the catheter follows the smaller-diameter of two branch vessels.

Following the path illustrated in FIG. 9, the next branch point encountered is at 136, where the vessel path follows the smaller-diameter branch vessel 148, as illustrated in detail in Example 9. Here the balloon is in a preferably non-inflated state, to reduce the tendency of the catheter end to be carried in to the larger-diameter vessel. At this branch point, the guide wire is torqued to orient the wire's bent tip in the direction of vessel 148, and the wire is then advanced, preferably independently of the catheter, into the smaller vessel. The catheter may now be threaded along the guide wire, and the device advanced as a unit until the next branch point is reached. Further catheter advance is achieved by guide wire or balloon-flow guidance, as above. It will be appreciated that the guide wire may be used to advance the catheter through branch points in which the selected path may follow either a larger or smaller-diameter branch vessel. That is, balloon-assisted flow guidance need not be used for accessing a larger-diameter branch vessel. Of course, with smaller-diameter branch vessels, the guide wire must generally be employed.

The method of the invention may also include the use of the balloon catheter to dilate a constricted vessel, particularly, where the constriction is encountered along a vessel path, and makes advance along the path more difficult. This is done simply by locating the balloon at a region of spastic constriction, and manipulating the device to inflate the balloon.

Once the target site is reached, the guide wire may be removed in order to open the inner lumen of the catheter, and thereby increase the rate of supply to the target site of a therapeutic, vasoocclusive, and/or radioopaque material. Alternatively, where the purpose of the targeting is to dilate the vessels or ducts at the target site, for example, to widen the lumen of a narrowed target vessel, either for angioplasty or spasm relaxation, the catheter device may be manipulated to inflate and deflate the balloon repeatedly. As indicated above, it may be advantageous to provide for complete valve closure at a selected guide wire position, to allow for greater balloon inflation pressure.

From the foregoing, it will be appreciated how various objects and features of the present invention are met. The catheter device takes advantage of both guide-wire and balloon-flow guidance for movement along small-diameter tortuous vessel or duct paths, to allow more efficient and in some cases more versatile catheter targeting to a tissue site.

The balloon in the device can also be used for relaxing spasmodic vessel walls, and for vessel wall therapies, such as plaque compression requiring balloon inflation. In this application, the catheter allows access to tortuous-path soft tissue target sites, and the ability to inflate the balloon to moderately high pressures, in contrast to prior-art slow-leak balloon catheters. Alternatively, where the catheter device is used to deliver a fluid agent to the target site, the guide wire can be withdrawn to increase the lumen cross section.

It will be clear from the foregoing that various changes and modifications in both the catheter device and tissue accessing method of the invention can be made without departing from the invention.

It is claimed:

1. A catheter device for accessing an internal tissue site along a vessel path from an external body access site, comprising
    a catheter having an inner lumen extending between proximal and distal ends, an inflatable balloon disposed adjacent the distal end, means communicating the catheter lumen with the balloon,
    a guide wire having proximal and distal ends and carried in said catheter for axial sliding movement therein,
    an annular ring mounted within the lumen distal to the communicating means, said ring defining an aperture through which the guide wire is received and which when partially blocked causes fluid supplied through the lumen to be forced into the balloon,
    valve means defined by said aperture and an annular enlargement on the guide wire dimensioned to partially block the aperture when the enlargement is advanced against the ring.

2. The device of claim 1, wherein the guide wire includes a radial enlargement effective to completely block said aperture at a selected guide wire position within the catheter.

3. The device of claim 1, wherein the catheter is formed of a tube which has an intermediate inflatable section forming said balloon, and said ring is positioned within the tube, distal to said inflatable section.

4. The device of claim 1, wherein the catheter is formed of a tube having an inflatable distal end section which forms said balloon, and said ring is positioned within the inflatable end section.

5. The device of claim 1, which further includes means attached to the proximal end of the guide wire for torquing the wire along its axis, to orient the distal end of the wire in a selected direction.

6. A method of accessing an internal body site along a narrow-vessel tortuous path which includes some branch points in which the path follows the larger-diameter of two branch vessels, and some in which the path follows the smaller diameter of two branch vessels, said method comprising, providing a catheter device composed of (a) a catheter having an inner lumen extending between proximal and distal ends, an inflatable balloon disposed adjacent the distal end means communicating the catheter lumen with the balloon, and means defining an aperture disposed distally to the communicating means such that when the aperture is partially blocked, fluid supplied through the lumen is forced into the balloon, (b) a guide wire having proximal and distal ends and carried in said catheter for axial sliding movement therein, and (c) valve means defined by said aperture and guide wire designed to partially block the aperture at one or more selected guide wire positions, to permit the catheter balloon to be inflated by supplying fluid through the catheter lumen at a rate greater than fluid escape through the partially blocked aperture,
    advancing the wire along the path,
    when a branch point at which the vessel path follows the larger-diameter of two branch vessels is reached, placing the guide wire axially in a position effective to partially block said aperture, and infusing fluid through the catheter to inflate the balloon, whereby the distal end of the catheter can be carried by fluid flow into the larger-diameter vessel, and
    when a branch point at which the vessel path follows the smaller diameter of two branch vessels is reached, placing the said guide wire to orient the guide wire distal end in the direction of the smaller-diameter vessel, and advancing the catheter into such vessel.

7. The method of claim 6, which further includes inflating said balloon when the catheter distal end encounters a region of vessel constriction, thereby to extend and relax the constricted vessel region and facilitate movement of the catheter device therethrough.

8. The device of claim 1 wherein the enlargement is located proximal to the ring.

9. The device of claim 1 wherein the enlargement is located distal to the ring.

10. The device of claim 1 wherein said inner lumen is a single inner lumen.

11. The device of claim 1 wherein the internal tissue site along a vessel path is accessed for the purpose of dilating the vessel at said site.

* * * * *